(12) United States Patent
Corbett et al.

(10) Patent No.: US 11,364,373 B2
(45) Date of Patent: Jun. 21, 2022

(54) BLOOD PUMP HOUSING COMPONENT (71) Applicant: ABIOMED, Inc., Danvers, MA (US)

(72) Inventors: Scott C. Corbett, Danvers, MA (US); Zhongwei Qi, Danvers, MA (US); Kar Lee, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 158 days.

(21) Appl. No.: 16/937,023

(22) Filed: Jul. 23, 2020

(65) Prior Publication Data

US 2021/0030935 A1 Feb. 4, 2021

Related U.S. Application Data (63) Continuation of application No. 15/784,694, filed on Oct. 16, 2017, now abandoned, which is a (Continued)

(51) Int. Cl.
*A61M 60/205* (2021.01)
*A61M 60/40* (2021.01)
(Continued)

(52) U.S. Cl.
CPC ........ *A61M 60/205* (2021.01); *A61M 60/135* (2021.01); *A61M 60/148* (2021.01);
(Continued)

(58) Field of Classification Search
CPC .............. A61M 60/135; A61M 60/148; A61M 60/205; A61M 60/40; A61M 60/414;
(Continued)

(56) References Cited

U.S. PATENT DOCUMENTS 4,817,586 A 4/1989 Wampler
6,217,541 B1 4/2001 Yu
(Continued)

FOREIGN PATENT DOCUMENTS

JP 2002535047 A 10/2002
JP 2007501644 A 2/2007
(Continued)

OTHER PUBLICATIONS

Office Action corresponding to Canadian Application No. 2,947,984 dated Jun. 30, 2021 (7 pages).
(Continued)

*Primary Examiner* — George Manuel
(74) *Attorney, Agent, or Firm* — Botos Churchill IP Law LLP (57) ABSTRACT

Blood pump assemblies and methods of manufacturing and operating blood pump assemblies are provided. The blood pump assembly includes a pump and an impeller blade rotatably coupled to the pump. The blood pump assembly also includes a pump housing component sized for passage through a body lumen and coupled to the pump. The pump housing component includes a peripheral wall extending about a rotation axis of the impeller blade. The peripheral wall includes an inner peripheral wall surface and an outer peripheral wall surface. The peripheral wall also includes one or more blood exhaust apertures. Each blood exhaust aperture in the one or more blood exhaust apertures is defined by an inner aperture edge and an outer aperture edge. Each inner aperture edge is chamfered between the inner peripheral wall surface and the outer peripheral wall surface.

15 Claims, 6 Drawing Sheets

Related U.S. Application Data continuation of application No. 15/237,836, filed on Aug. 16, 2016, now Pat. No. 9,821,100, which is a continuation of application No. 14/711,143, filed on May 13, 2015, now Pat. No. 9,433,713.

(60) Provisional application No. 61/992,835, filed on May 13, 2014.

(51) Int. Cl.
| | |
|---|---|
| *F04D 3/00* | (2006.01) |
| *F04D 7/00* | (2006.01) |
| *F04D 29/18* | (2006.01) |
| *F04D 29/52* | (2006.01) |
| *F04D 29/64* | (2006.01) |
| *C25F 3/16* | (2006.01) |
| *A61M 60/135* | (2021.01) |
| *A61M 60/148* | (2021.01) |
| *A61M 60/857* | (2021.01) |
| *A61M 60/414* | (2021.01) |

(52) U.S. Cl.
CPC .......... *A61M 60/40* (2021.01); *A61M 60/857* (2021.01); *C25F 3/16* (2013.01); *F04D 3/005* (2013.01); *F04D 7/00* (2013.01); *F04D 29/181* (2013.01); *F04D 29/528* (2013.01); *F04D 29/648* (2013.01); *A61M 60/414* (2021.01); *Y10T 29/49247* (2015.01)

(58) Field of Classification Search
CPC ...... A61M 60/857; C25F 3/16; F04D 29/181; F04D 29/528; F04D 29/648; F04D 3/005; F04D 7/00; Y10T 29/49247
See application file for complete search history.

(56) References Cited

U.S. PATENT DOCUMENTS

| | | |
|---|---|---|
| 2005/0113631 A1 | 5/2005 | Bolling et al. |
| 2006/0100565 A1 | 5/2006 | Aboul-Hosn |
| 2008/0114339 A1 | 5/2008 | McBride et al. |
| 2008/0269880 A1 | 10/2008 | Jarvik |
| 2010/0240964 A1* | 9/2010 | Sterling .......... A61B 5/150221 600/300 |
| 2010/0268017 A1 | 10/2010 | Siess |
| 2011/0313237 A1 | 12/2011 | Miyakoshi et al. |
| 2012/0321512 A1 | 12/2012 | Kawamura et al. |
| 2014/0336446 A1 | 11/2014 | Rodefeld |

FOREIGN PATENT DOCUMENTS

| | | |
|---|---|---|
| JP | 2010528797 A | 8/2010 |
| JP | 2010534080 A | 11/2010 |
| JP | 2011161147 A | 8/2011 |
| WO | 9834658 A1 | 8/1998 |
| WO | 0043053 A1 | 7/2000 |
| WO | 2008152425 A1 | 12/2008 |
| WO | 2009010888 A2 | 1/2009 |

OTHER PUBLICATIONS

International Search Report and Written Opinion in International Application No. PCT/US2015/030650 dated Jul. 30, 2015.

Fukushima K. et al., Visualization of thrombus formation process and flow analysis on shear blood flow, Seitai Ikougaku [Medical and Biological Engineering], Japan, 2007, vol. 45, No. 1, pp. 99-105.

Office Action corresponding to Japanese Patent Appl. No. 2019-119304 dated Jun. 1, 2020 (8 pages).

Office Action from corresponding Japanese Patent Application No. 2019-119304 dated Nov. 17, 2021 (8 pages).

* cited by examiner

Rotatably Couple Impeller Blade to Pump

904

Couple Pump to Pump Housing Component, the Pump Housing Component Including a Peripheral Wall Extending About a Rotation Axis of the Impeller Blade, the Peripheral Wall Including an Inner Surface and an Outer Surface Positioned Radially Outward of the Inner Surface with Respect to the Rotation Axis of the Impeller

906

Form Plurality of Blood Exhaust Apertures in the Peripheral Wall, each Blood Exhaust Aperture Defined by an Inner Edge and an Outer Edge, the Inner Edge Including One of a Rounded Edge Portion and a Chamfered Edge Portion

FIG. 9

BLOOD PUMP HOUSING COMPONENT

CROSS-REFERENCE TO RELATED APPLICATIONS

This application is a continuation of U.S. patent application Ser. No. 15/784,694, filed on Oct. 16, 2017, which is a continuation of U.S. patent application Ser. No. 15/237,836, filed Aug. 16, 2016, now U.S. Pat. No. 9,821,100, which is a continuation of U.S. patent application Ser. No. 14/711,143, filed May 13, 2015, now U.S. Pat. No. 9,433,713, which claims priority to U.S. Provisional Patent Application No. 61/992,835, filed May 13, 2014, the entire disclosures of which are hereby incorporated herein by reference.

TECHNICAL FIELD

The present disclosure relates to blood pump assemblies. More specifically, the present disclosure relates to a housing component of a blood pump assembly.

BACKGROUND

A blood pump assembly, such as an intracardiac blood pump assembly, is introduced in the heart to deliver blood from the heart into an artery. Blood pump assemblies pull blood from the left ventricle of the heart and expel blood into the aorta. The blood pump assemblies may be introduced percutaneously during a cardiac procedure through the vascular system. Specifically, the pump assemblies can be inserted via a catheterization procedure through the femoral artery, into the ascending aorta, across the valve and into the left ventricle. The pumping of blood via a blood pump assembly can damage the blood or cause hemolysis as the blood is drawn through the blood pump assembly.

SUMMARY

Devices and methods of manufacture and implementation described herein provide blood pump assemblies with housing components designed to reduce hemolysis and damage to blood. The blood pump housing includes blood exhaust apertures designed to expel the blood. The blood exhaust apertures have inner edges which are blunted with a chamfer or a round. Blunting the inner edge of the aperture causes a significant reduction in hemolysis. The use of chamfered inner edges on the blood exhaust apertures allows the blood to follow a flow pattern in which the shear stresses may be decreased compared to flow past sharp or unblunted edges. This causes fewer red blood cells to be ruptured as the blood flows through the cannula and out through the blood pump housing, resulting in lower hemolysis. For example, the use of charmfered inner aperture edges in the blood pump housing can reduce markers of hemolysis by over 50% compared to standard aperture edges.

In some implementations, non-adjacent inner and outer edges of the blood pump housing are chamfered. This reduces the profile of struts of the blood pump housing component orthogonal to the direction of the blood exiting the blood pump housing. Such a chamfer configuration significantly reduces shear stress induced in blood exiting the aperture and decreases the area of wakes induced in the blood flow by the pump housing struts. These effects may reduce hemolysis in blood flow through the blood pump housing.

In some implementations the chamfered edge may include a chamfer of 45°. In some implementations the chamfered edge may include a chamfer of 10°, 20°, 30°, 40°, 50°, >50°, or any other suitable angle. In some implementations the chamfered inner edge may include an alternate chamfer with two chamfered edges being substantially parallel to the flow of blood through the aperture such that the two edges are positioned opposite one another on a strut. In some implementations the inner edge of the aperture instead or in addition to being chamfered may be rounded or alternately chamfered. In some implementations the rounded edge may include a radius ranging from 40 microns to 105 microns. In some implementations the aperture edge may be rounded only in some locations.

Various implementations provide blood pump assemblies and methods of manufacturing blood pump assemblies. In one aspect, a blood pump assembly includes a pump and an impeller blade rotatably coupled to the pump. The blood pump assembly also includes a pump housing component sized for passage through a body lumen and coupled to the pump. The pump housing component includes a peripheral wall having an inner surface and an outer surface. The peripheral wall includes one or more blood exhaust apertures. Each blood exhaust aperture defined by an inner edge and an outer edge. Each inner edge of the blood exhaust aperture includes a chamfered portion between the inner surface and the outer surface.

In some implementations, the blood pump assembly includes an inner edge including a chamfer of about 45°. In other implementations, the blood pump assembly includes an outer edge which is rounded between the inner wall surface and the outer surface. In particular implementations, the rounded outer edge has a radius of 40 microns or greater. In other implementations, the rounded outer edge has a radius of 105 microns or greater. In some implementations, the blood pump assembly has an outer edge which is rounded in its entirety. The blood pump assembly may be electropolished, mechanically polished or polished in any other suitable way. In some implementations, the blood pump assembly includes an inner edge with a first chamfered portion having a first chamfer angle and a second chamfered portion having a second chamfer angle greater than the first chamfer angle. The blood pump assembly may include an impeller blade positioned at least in part in the pump housing component. The blood pump assembly may include a pump housing component coupled to the pump at a first end and coupled to a cannula at a second end opposite the first end. The cannula component includes a blood inlet manifold. In some implementations, the blood pump assembly also includes a pigtail extension coupled to the blood inlet manifold.

In another aspect, a blood pump assembly includes a pump and an impeller blade rotatably coupled to the pump. The blood pump assembly also includes a pump housing component sized for passage through a body lumen and coupled to the pump. The pump housing component includes a peripheral wall having an inner surface and an outer surface. The peripheral wall includes a plurality of struts. Each strut has a first and second inner edge and a first and second outer edge. Each first inner edge and second outer edge are chamfered between the inner surface and the outer surface wherein the first inner edge and the second inner edge are non-adjacent. The peripheral wall also includes one or more blood exhaust apertures. Each blood exhaust aperture is disposed between a pair of the plurality of struts.

In some implementations, each first inner edge and each second outer edge of the plurality of struts has a chamfer angle of about 45°. The blood pump assembly may be electropolished, mechanically polished, hand-polished or polished by any suitable method. The blood pump assembly includes an impeller blade positioned at least in part in the pump housing component. The pump housing component is coupled to the pump at a first end. The pump housing component is coupled to a cannula component at a second end opposite the first end. In some implementations, the cannula component includes a blood inlet manifold. The blood pump assembly may include a pigtail extension coupled to the blood inlet manifold.

In another aspect, a method of manufacturing a blood pump assembly includes rotatably coupling an impeller blade to a pump. The method also includes coupling the pump to a pump housing component. The pump housing component includes a peripheral wall extending about a rotation axis of the propeller blade. The peripheral wall includes an inner surface and an outer surface positioned radially outward of the inner surface with respect to the rotation axis of the impeller. The method also includes forming a plurality of blood exhaust apertures in the peripheral wall. Each blood exhaust aperture is defined by an inner edge and an outer edge. The inner edge of the blood exhaust aperture includes a rounded edge portion and a chamfered edge portion.

In some implementations, the method of coupling the pump to the pump housing components includes positioning the impeller blade rotatably coupled to the pump at least in part within the pump housing component. In some implementations, forming the plurality of blood exhaust apertures includes forming the outer edge by a tumbling process. In certain implementations, the outer edge is formed by a rolling process or by removing a right-angled edge. In some implementations, forming the plurality of blood exhaust apertures includes rounding the entirety of the outer aperture edge between the inner surface and the outer surface. In certain implementations, the inner edge is rounded or chamfered by a tumbling process, a rolling process, or any other suitable method for removing a right-angled edge. In some implementations, the pump housing component is coupled to the pump at a first end of the pump housing component and a cannula component is coupled to the second end of the pump housing component opposite the first end. The cannula component includes a blood inlet manifold. In some implementations a pigtail extension may be coupled to the blood inlet manifold. In some implementations the pump housing component is electropolished.

In another aspect, a method of operating a blood pump assembly includes rotating an impeller about a rotation axis to draw blood into a cannula portion of a blood pump assembly at a blood inlet manifold using a pump motor coupled to the cannula portion by a pump housing component and expelling blood from the blood pump assembly via a plurality of blood exhaust apertures in the peripheral wall. The pump housing component includes a peripheral wall extending about the rotation axis of the impeller blade. The peripheral wall includes an inner peripheral wall surface and an outer peripheral wall surface positioned radially outward of the inner peripheral wall surface with respect to the rotation axis. Each blood exhaust aperture in the plurality of blood exhaust apertures is defined by an inner aperture edge and an outer aperture edge, the inner aperture edge including a chamfered edge portion chamfered between the inner peripheral wall surface and the outer peripheral wall surface. In some implementations, the impeller blade is positioned at least in part in the pump housing component. In certain implementations, the blood inlet manifold includes a plurality of inlet openings. In some implementations, the method further comprises coupling a pigtail extension to the blood inlet manifold.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof may be combined or integrated in other systems. Moreover, certain features may be omitted or not implemented.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and implementations of, inventive systems and methods of providing a blood pump assembly. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

The systems, devices, and methods described herein reduce hemolysis and similar blood damage resulting from blood flow through the blood pump. By adjusting the aperture edges of the blood pump housing or making additional adjustments to the housing to ensure proper positioning, among other design aspects, occurrence of hemolysis with use of the blood pump assembly is decreased.

Figure 1:
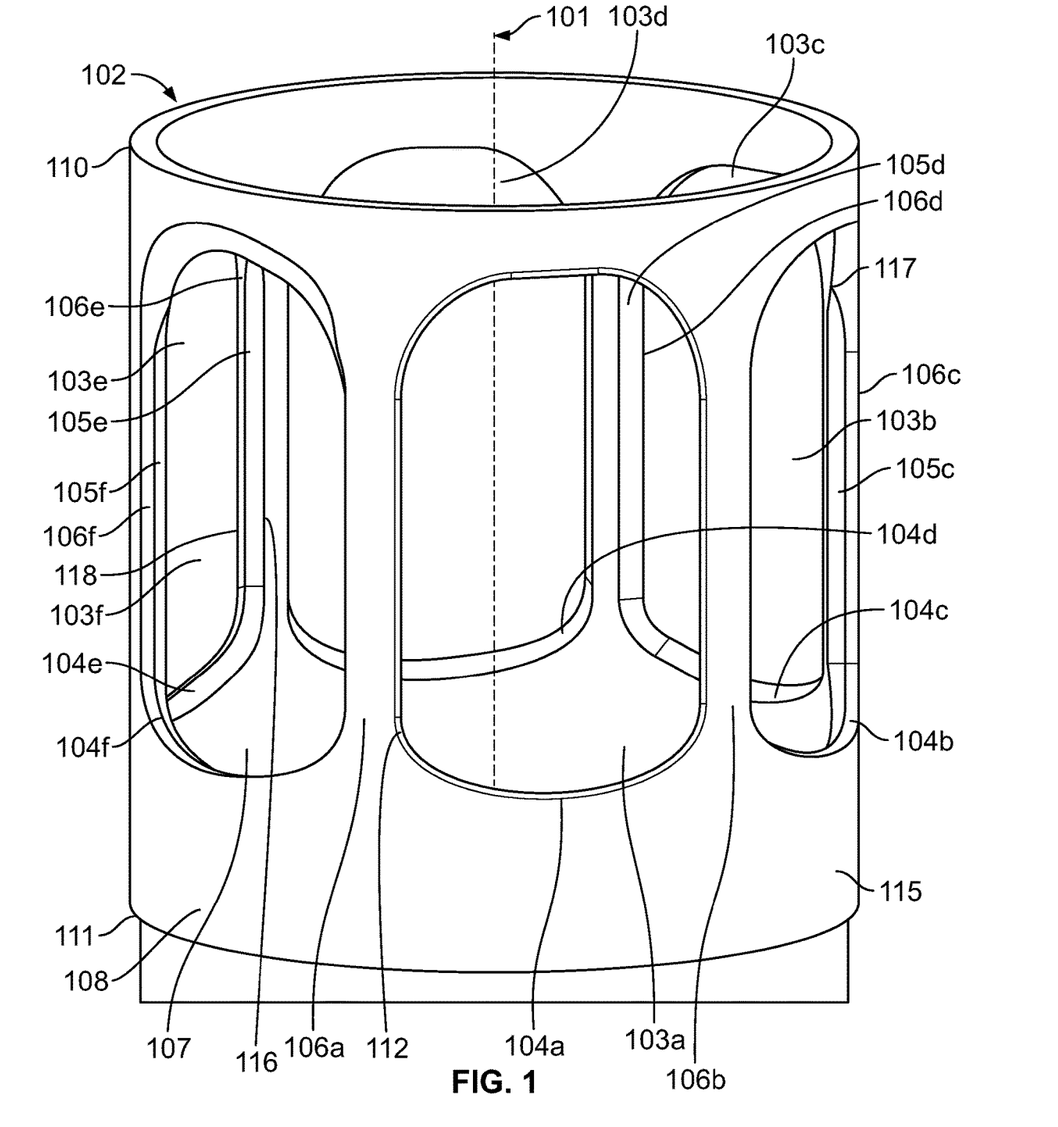
FIG. 1 shows a perspective view of a blood pump housing component including chamfered edges, in accordance with example implementations.

FIG. 1 shows a view of a blood pump housing component 102 including chamfered inner edges 105c-f, in accordance with example implementations. The pump housing component includes an upstream end 110, a downstream end 111, a peripheral wall 115, an inner surface 107, an outer surface 108, a plurality of circumferential aperture surfaces 104 which span between the inner surface 107 and the outer surface 108, inner edges 116 and outer edges 118 which define blood exhaust apertures 103a-f, and struts 106a-f. The downstream end 111 of the pump housing component 102 is configured for coupling to a pump (not shown) and the upstream end 110 is configured for coupling to a cannula (not shown). In some implementations, the pump housing component 102 is configured to encapsulate a pump and to house an impeller rotatably coupled to the pump. The peripheral wall 115 of the pump housing component 102 has a substantially cylindrical shape and extends about an axis 101 from the downstream end 111 to the upstream end 110. In some implementations, the axis 101 is the axis of rotation of an impeller rotatably coupled to a microaxial pump coupled to the pump housing component 102 and positioned in the pump housing component 102. The blood exhaust apertures 103a-f are configured to expel blood drawn into the cannula coupled to the pump housing component via a pump and an impeller coupled to the pump. Although six apertures are shown, any suitable number of apertures may be included (e.g., 2, 3, 4, 5, 7, 8, 10, >10, or any suitable number). While the blood exhaust apertures 103a-f include apertures having rounded corners 112a-f, in some implementations the apertures may include a round aperture, a circular aperture, or apertures of any suitable shape. The blood exhaust apertures 103a-f extend through the peripheral wall 115 of the pump housing component 102 from the inner surface 107 to the outer surface 108. The circumferential aperture surfaces 104a-f of the blood exhaust apertures 103a-f include rounded edge portions 105a-f, respectively. The rounded edge portions 105a-f may include the inner edge 116 formed by the inner surface 107 and the circumferential aperture surfaces 104a-f. The rounded edge portions 105 a-f may include the outer edge 118 formed by the outer surface 108 and the circumferential aperture surfaces 104a-f instead or in addition to including the inner edge 116. The rounded edge portions 105a-f may extend from the inner surface 107 to the outer surface 108. The inner edge 116 or the outer edge 118 of the blood exhaust apertures 103a-f are chamfered to form chamfered surfaces 105c-f. In certain implementations, the chamfered surfaces 105c-f are bounded on one or both sides by a lark's tongue 117. In some implementations, the circumferential aperture surfaces 104a-f are rounded along the entire inner edge 116 or outer edge 118. In certain implementations, the circumferential aperture surface 104a-f is rounded along only a portion of the inner edge 116 or outer edge 118. The struts 106a-f are positioned between the blood exhaust apertures 103a-f along a portion of the circumferential aperture surfaces 104a-f. In some implementations, the struts 106a-f positioned between blood exhaust apertures 103a-f vary in geometry as a result of the size, number and distribution of the blood exhaust apertures 103 a-f and of the rounded or chamfered edge 105c-f of the blood exhaust apertures 103a-f. The geometries of the struts 106 may also vary according to the curvature or chamfer alterations to the inner edge 116 and the outer edge 118.

The pump housing component 102 may be composed of a metal. In some implementations, the pump housing component 102 is electropolished. The rounded edge portions 105a-f of circumferential aperture surfaces 104a-f may be formed via tumbling, rolling, machining, or any other suitable material removal process, such that the circumferential aperture surfaces 104a-f are rounded, at least in part, in a region between the inner surface 107 and the outer surface 108. Prior to rounding a portion of the inner edge 116 or the outer edge 118, the circumferential aperture surface 104a-f and the inner surface 107 or outer surface 108 may include an edge configured at a 90-degree angle or chamfered. Accordingly, the circumferential aperture edge may be rounded or chamfered to remove a right-angled edge.

Figure 2:
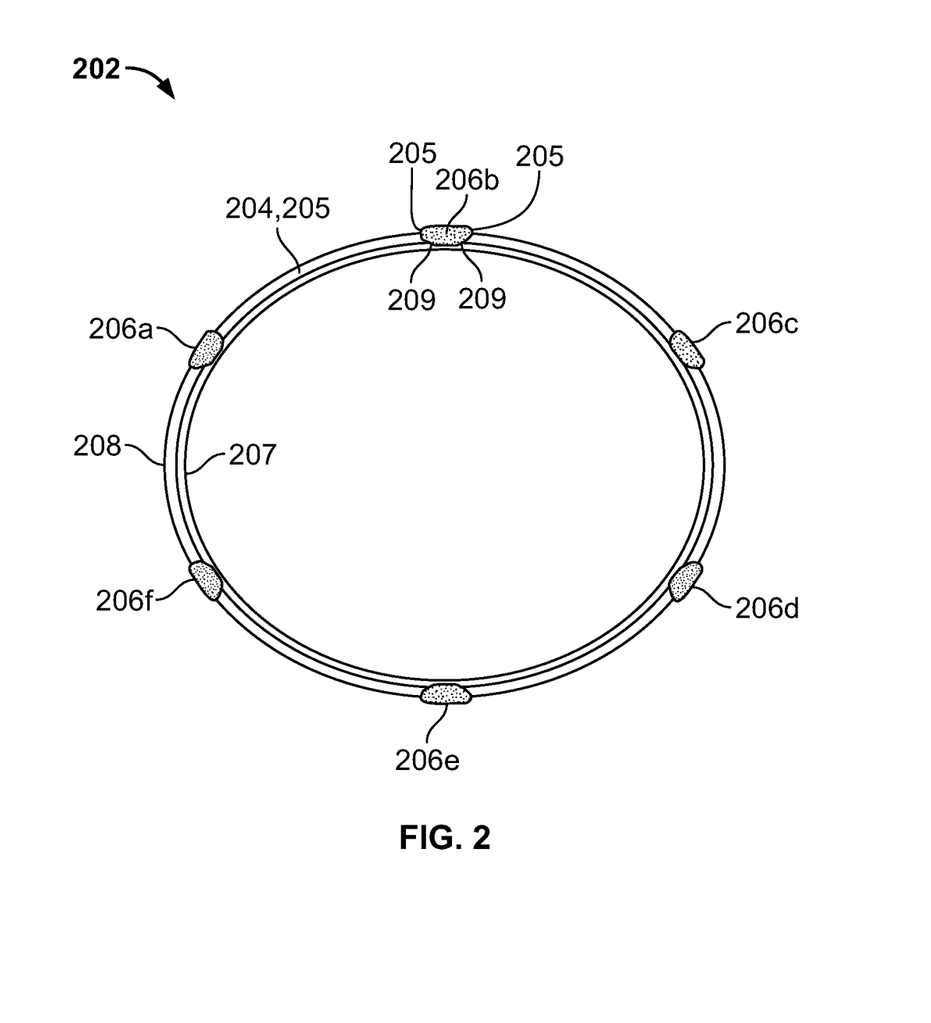
FIG. 2 provides a top cross-sectional view of an impeller including rounded edges and chamfered edges, in accordance with example implementations.

FIG. 2 provides a top cross-sectional view of a blood pump housing component 102 including rounded edges, in accordance with example implementations. As shown in FIG. 1, the blood exhaust apertures defined cross-sectionally by the struts 206a-f include inner chamfered edges 209a-f and rounded outer edges 205a-f. In example implementations, the inner edge and the outer edge may both be chamfered, both rounded, or the inner edge may be rounded and the outer edge may be chamfered. In some implementations, the inner edge may have a radius including, but not limited to, 40 microns. In some implementations, the outer edge may have a radius including, but not limited to, 105 microns.

FIGS. 3-6 show results of computational tests of the shear stresses associated with blood flow around struts having different cross-sectional geometries. Each figure depicts the flow of blood from the interior of the blood pump housing 102 through the blood exhaust apertures 103 past a strut 106 such that the perspective shown in FIGS. 3-6 is corresponds to a portion of the cross-sectional view depicted in FIG. 2. In each figure, the flow of blood is generally from the left to right, from the interior of the blood pump housing to the exterior. As depicted, the blood is not exhausted purely radially from the interior of the blood pump housing, but also has a significant tangential velocity component. The direction of blood flow and the shear stress felt at each point are depicted in each figure by arrows. The magnitude of the shear stress at each point is indicated by the shading of the arrows. Lighter shading indicates lower shear stress, and darker shading indicates higher shear stress.

Figure 3:
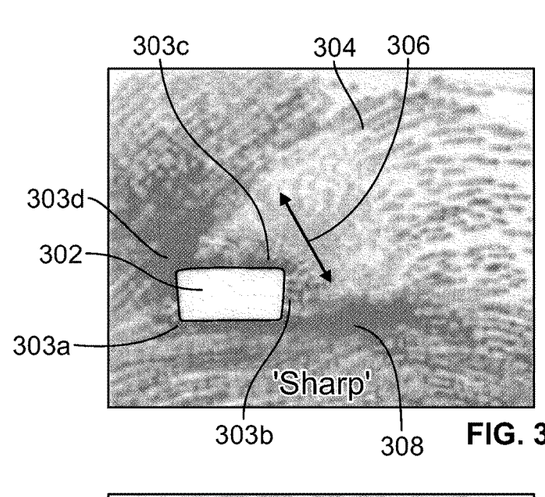
FIGS. 3-6 show the shear stresses associated with blood moving past pump housing struts of different cross-sectional geometries.
Figure 4:
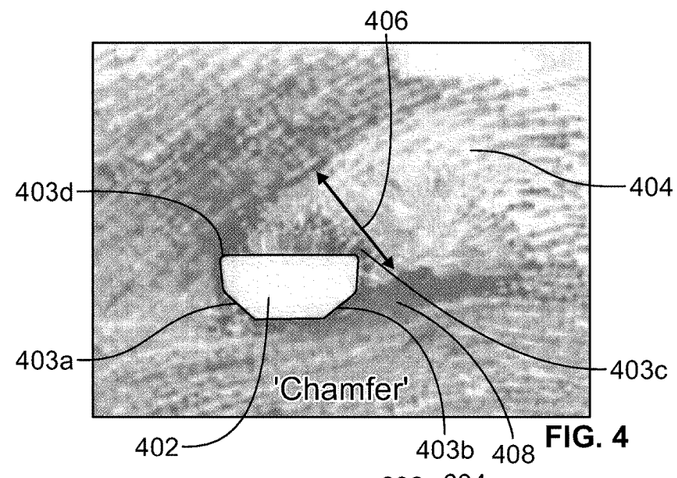
Figure 5:
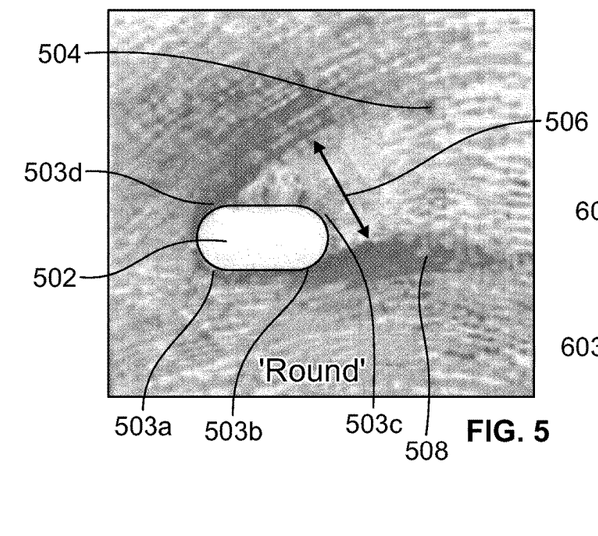
Figure 6:
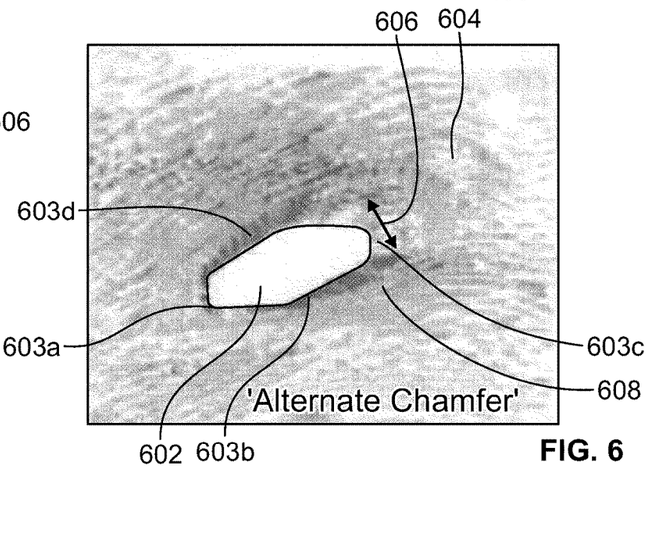

FIG. 3 shows a strut cross section 302 having sharp corners 303a-d and shedding a wake 304 having a width 306. The strut cross section 302 creates a relatively high stress region 308 in the blood flow. FIG. 4 shows a strut cross section 402 having chamfered corners 403 a-b and sharp corners 403c-d. The strut cross section 402 sheds a wake 404 having a width 406 and creates a relatively high stress region 408 in the blood flow. FIG. 5 shows a strut cross section 502 having rounded corners 503a-d and shedding a wake 504 having a width 506. The strut cross section 502 creates a relatively high stress region 508 in the blood flow. FIG. 6 shows a strut having a cross section 602 with chamfered corners 603a-b and sharp corners 603c-d in which corners 603a and 603b are not adjoining corners. The strut cross section 602 sheds a wake 604 having width 606. The strut cross section 602 creates a region of elevated shear stress 608 in the blood flow. As depicted in FIGS. 3-6, the cross-sectional shape of the struts impacts the shear stresses and direction of the flow of blood out of the blood exhaust apertures. This is because blood flowing from inside the blood pump housing to outside the blood pump housing encounters the struts and must flow around the struts. This results in the areas 308, 408, 508, 608 of large stresses as the blood divides around the strut. Additionally, this causes the wakes 304, 404, 504 and 604 behind the struts. The size of each wake may correspond to the disruption of the flow pattern induced by each strut geometry. Reduced shear stresses on the red blood cells exiting the blood pump housing leads to a less traumatic flow pattern, thus decreasing the likelihood of blood cell damage and rupture e.g., hemolysis). This may also allow blood cells to maintain their shape and elasticity without cellular rupture.

As depicted in FIGS. 3-6, different strut geometry causes different flow patterns and associated stresses. The strut cross-section 302 causes relatively large flow disruption due to its right-angled corners 303a-d. The high stress region 308 along the bottom edge of the strut cross-section 302 indicates an area of high pressure where blood is being forced to deviate from its path as it travels along the long side of the strut on the interior of the blood pump housing and around the sharp corner 303 d of the strut 302 through the blood exhaust aperture. The wake 304 behind the strut outside of the blood pump housing is large compared to the size of the strut 302. The strut cross section 502 having rounded corners 503a-d has a similar region of relatively high stress 508 as blood flows around the strut and out the blood exhaust aperture. The wake behind the round strut 504 outside of the blood pump housing has a width less than that of strut 302. The chamfered strut 402 has an area of high stress 408 as well as a relatively large wake behind the strut 404 indicating that the geometry results in relatively large interruption to the blood flow, The strut cross-section 602 causes reduced flow interruption resulting in lower shear stresses compared to strut cross sections 302, 402 and 502 (e.g., 10% lower, 20% lower, 30% lower, or less), There is a relatively small area of elevated shear stress 608 as the blood travels around the strut and through the blood exhaust aperture due to the sharp leading edge 603c that is directed toward the interior of the blood pump housing and chamfered edges 603a-b which are substantially parallel to the flow of blood out of the blood pump housing. The wake 604 downstream from the strut 602 is relatively small (e.g., about 50%, 30%, 20%, or <20% the size of the wake 304) with only relatively small areas of disrupted flow. Thus, the chamfer geometry of strut 604 results in relatively low flow disruption which may reduce hemolysis compared to strut cross sections 302, 402 and 502.

Figure 7:
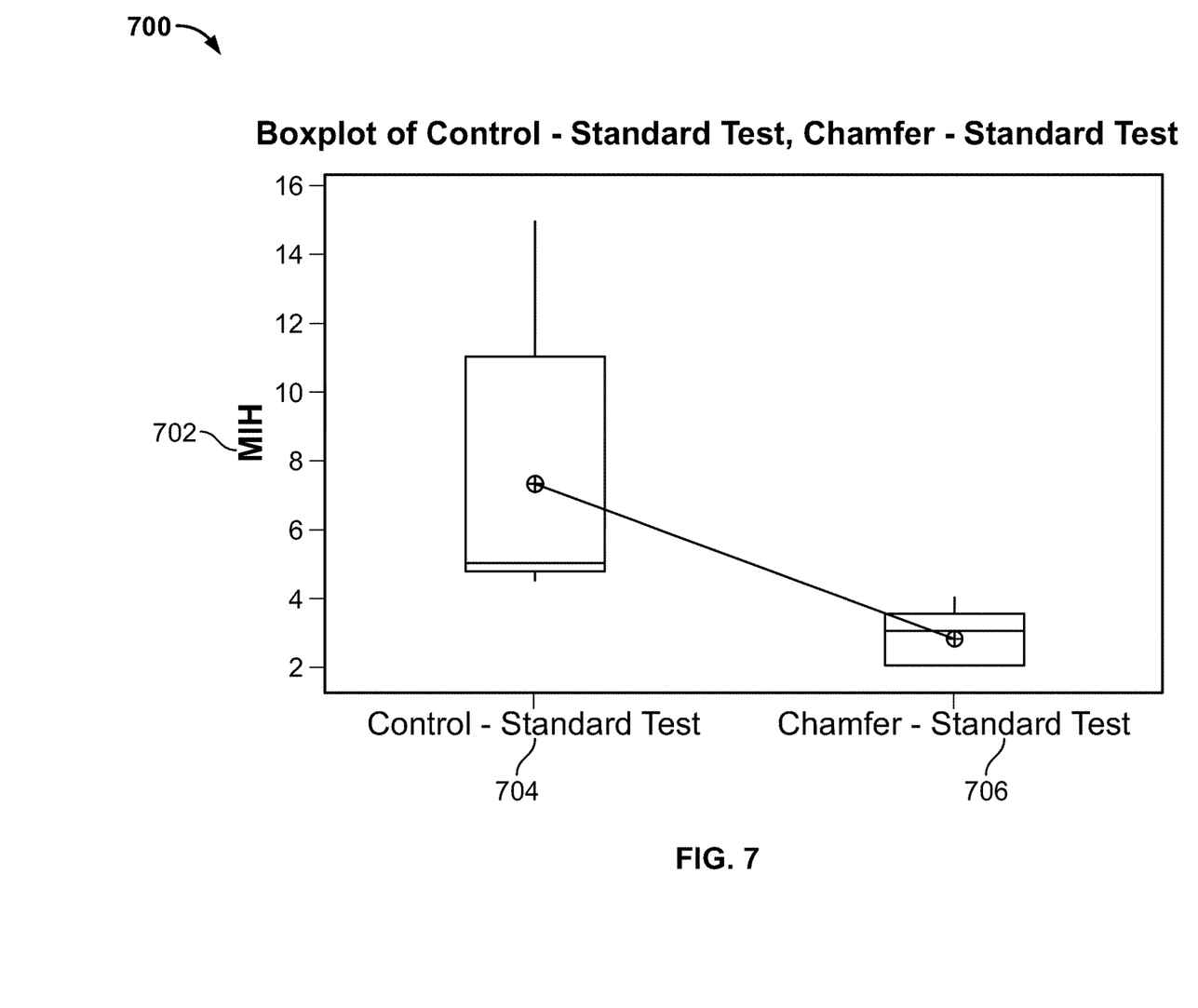
FIG. 7 shows a boxplot displaying hemolysis reduction associated with chamfered housing components.

FIG. 7 shows a boxplot 700 comparing the results of hemolysis testing of a blood pump assembly having standard right-angled blood exhaust aperture edges 704 and a blood pump assembly having chamfered inner aperture edges 707 such that the cross-sectional strut geometry is similar to the geometry depicted in FIG. 4. The blood pump assembly having right-angled blood exhaust aperture edges was electropolished. The blood pump assembly having chamfered edges created by machining was electropolished and tumbled. The blood pump assemblies were identical in all ways besides the blood exhaust aperture geometries and the method of forming these geometries. The blood pump assembly having right-angled blood exhaust apertures and the blood pump assembly having chamfered blood exhaust apertures were installed in identical Hemolysis Mock Loops, Part Number 0046-6667, The loop draws blood from a main blood pool warmed to 37° C.±2° C. by a water bath. The blood is pumped through the blood pump housing by the blood pump with a maintained differential pressure. The conditions chosen for the test are chosen to represent the worst case conditions expected during device operation. The hemolysis testing was conducted according to ASTM Standard F 1841-97 (2005). Plasma free hemoglobin concentration and Hematocrit were evaluated at the beginning and end of testing according to the Cyano-hemoglobin technique. The y-axis 702 represents the modified index of hemolysis (MIH), which is the amount of hemoglobin released into the plasma normalized by the hemoglobin contained in the total amount of blood pumped through the device. The boxplot 700 shows that the average MIH is decreased over 50% with the use of the chamfered edge compared to standard right-angled blood exhaust apertures. Thus, hemolysis is significantly reduced by use of the chamfered aperture design, even without altering the impeller blade geometry or other pump design aspects.

Figure 8:
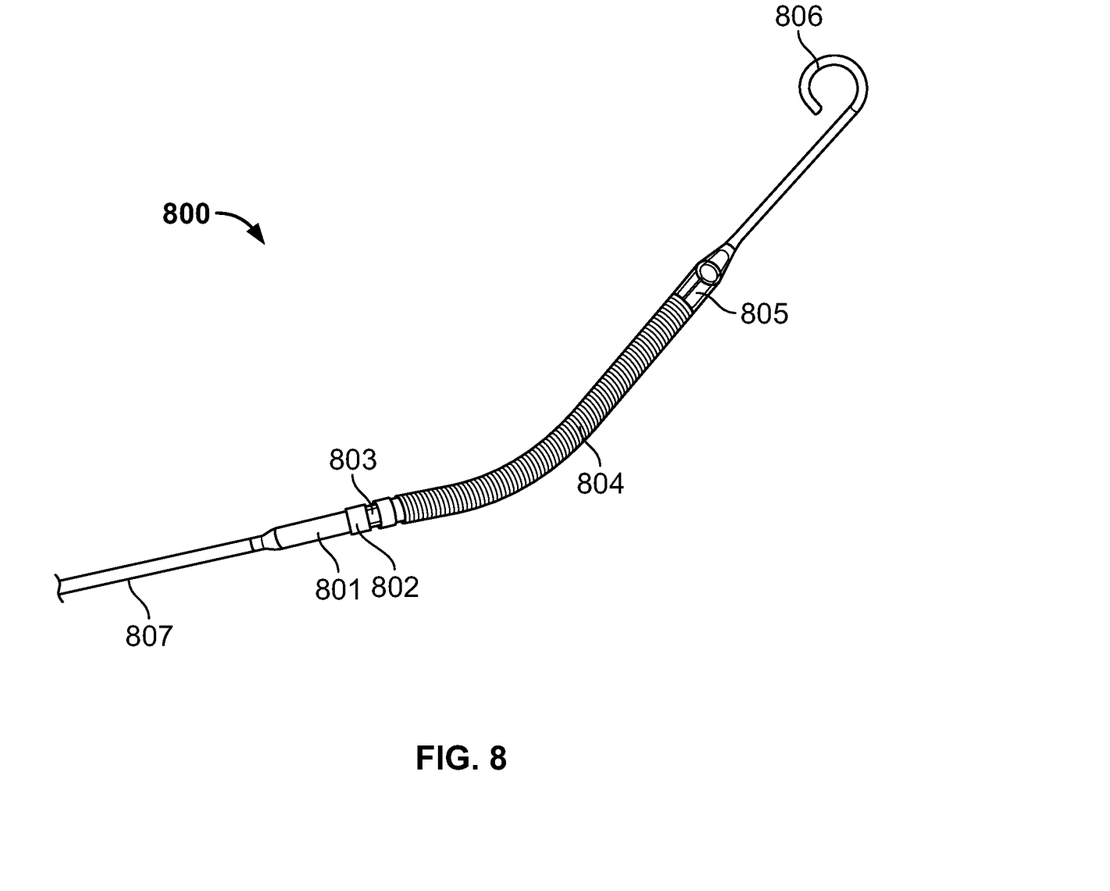
FIG. 8 shows a perspective view of a blood pump assembly, in accordance with example implementations.

The aforementioned blood pump housing components can be incorporated into a blood pump assembly. FIG. 8 shows such a blood pump assembly 800, according to certain implementations. The blood pump assembly 800 includes a blood pump 801, a housing component 802, an impeller blade 803, a cannula 804, a blood inlet manifold 805, and a pigtail extension 806. The blood pump 801 is coupled to the cannula 804 via the housing component 802. The features of the housing component are similar to those of the housing components 102 and 202 of FIGS. 1 and 2, respectively. The housing component 802 includes one or more apertures 103 having an inner edge 116 and an outer edge 118. In some implementations, either or both of the inner edge 116 and the outer edge 118 may include a rounded edge portion or a chamfered edge portion 105, which helps to reduce hemolysis. The rounded edge portion or the chamfered edge portion may be obtained through machining a chamfer or a radius or via a tumbling process, in accordance with some implementations. The chamfered edge portion may include a symmetrical chamfer or an asymmetrical chamfer. The chamfer may include, but is not limited to a 45° chamfer.

The blood pump assembly 801 includes a catheter 807 coupled to the blood pump 801. In some implementations, the blood pump 801 includes a motor. In such cases, the catheter 807 may house electrical lines coupling the pump motor to one or more electrical controllers or other sensors. In certain implementations, the blood pump is driven by a pump portion external to the patient (e.g., via a flexible drive shaft). The catheter 807 may also house other components, such as a purge fluid conduit, or other conduits configured to receive a guidewire. The housing component 802 includes one or more apertures or openings configured to expel or exhaust blood drawn into cannula 804 out of the blood pump assembly 800. In some implementations, the housing component 802 encapsulates the blood pump 801. In some implementations, blood pump 801 includes a micro-axial pump having a pumping capability, including, but not limited to, a range of 5 L/min and 2.5 L/min. In some implementations, blood pump 801 includes a micro axial pump having a diameter including, but not limited to, a range of 21 Fr to 10 Fr.

Blood pump 801 includes an impeller blade 803 rotatably coupled to the blood pump 801. The cannula 804 may include an elongated flexible hose portion and may include a shape memory coil, such as a nitinol coil. In some implementations, the cannula 804 is composed, at least in part, of a polyurethane material. In some implementations, the cannula 804 has a diameter including, but not limited to, a range of 12 Fr to 9 Fr. In some implementations, cannula 804 includes a 45° bend. The cannula 804 includes a blood inlet manifold 805 coupled to the cannula 804 at a proximal end of the cannula 804 to receive blood flow into the blood pump assembly 800. The blood inlet manifold 805 includes one or more blood inlet openings positioned in the inlet manifold 805. The blood inlet manifold 805 couples a pigtail extension 806 to the cannula 804. In some implementations, the pigtail extension has a diameter of 6 Fr. In some implementations, the pigtail extension has a diameter in the range of 4-8 Fr.

The pigtail extension 806 assists with stabilizing and positioning the blood pump assembly 800 in the correct position in the left ventricle of a heart. In some implementations, the blood pump assembly 800 is inserted percutaneously through the femoral artery and into the left ventricle. When properly positioned, the blood pump assembly 800 delivers blood from the inlet area at the blood inlet manifold 805, which sits inside the left ventricle, through the cannula 804, to the outlet openings of the housing component 802 positioned in the ascending aorta.

In accordance with some implementations, the pigtail extension 806 is configurable from a straight configuration to a partially curved configuration. Accordingly, the pigtail extension 806 may be composed, at least in part, of a flexible material. In accordance with some implementations, the pigtail extension 806 has a dual stiffness. More specifically, in some implementations, the pigtail extension 806 includes a distal section 810 composed of a material that is softer or has a lower stiffness than proximal section 808 of the pigtail extension 806. The proximal section may be composed of a different material and have a different structure than the blood inlet manifold 805 and the cannula 804. The proximal section 808 may be stiff enough to substantially prevent section 808 from buckling, thereby keeping the blood inlet openings in the blood inlet manifold 805 out of the ventricle apex of the heart while reducing the probability of the blood outlet openings or blood exhaust apertures in the housing component 802 from moving into the aortic valve of the heart or into the ventricle of the heart. The distal section 810 of the pigtail extension 806 is flexible with respect to the proximal section 808, to provide an atraumatic tip for contact with the ventricle wall and to allow for guidewire loading. In some implementations, the proximal section 808 and the distal section 810 of the pigtail extension are composed of different materials having different stiffness. In sonic implementations, the proximal section 108 and the distal section 810 of the pigtail extension are composed of the same material having different stiffness.

Figure 9:
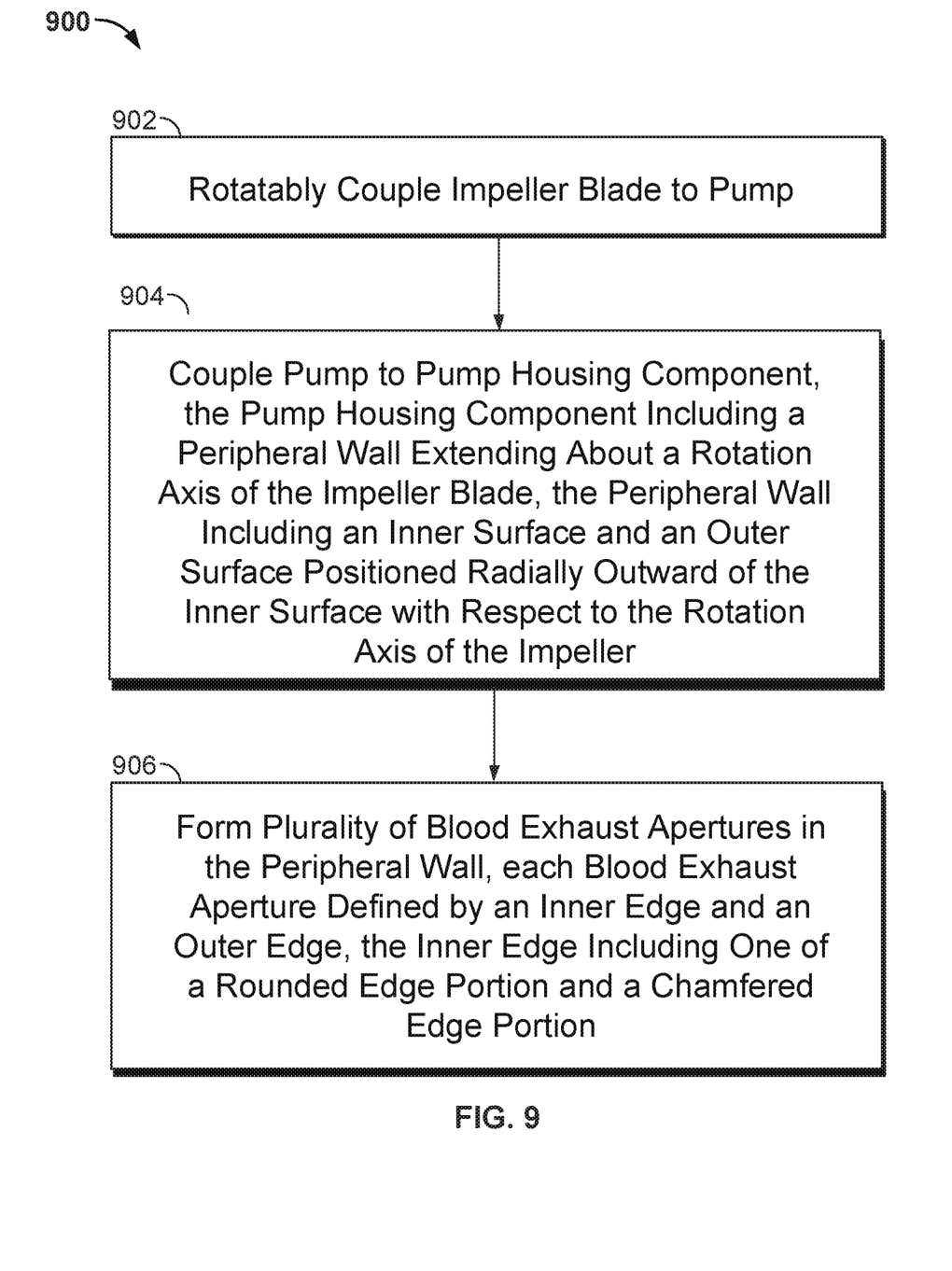
FIG. 9 depicts a method for manufacturing a blood pump assembly according to certain implementations.

FIG. 9 depicts a method 900 for the manufacture of a blood pump assembly according to certain implementations. The method 900 may be implemented to manufacture the blood pump assembly 800 in any of the aforementioned implementations including but not limited to blood pump assemblies having blood exhaust apertures with blunted edges which are rounded, chamfered, or some combination thereof, wherein the edge formed by the circumferential aperture surface and the inner surface, the circumferential aperture surface and the outer surface, or both may be blunted. The method 900 may be implemented for manufacture of blood pump assemblies having blood exhaust apertures with chamfered or rounded edges which are chamfered or rounded around the entirety of the circumferential edge and the inner or outer surface or only in some portions. The method 900 may be implemented for manufacture of blood pump assemblies having any number and size of blood exhaust apertures. In step 902, an impeller blade, such as impeller blade 803, is rotatably coupled to a blood pump, such as pump 801. In step 904, the blood pump is coupled to a pump housing, such as pump housing 802. The pump housing includes a peripheral wall extending about a rotation axis of the impeller blade, the peripheral wall including an inner surface and an outer surface positioned radially outward of the inner surface with respect to the rotation axis of the impeller. In step 906, a number of blood exhaust apertures, such as blood exhaust apertures 803, are formed in the wall of the blood pump housing 802. Each blood exhaust aperture in the plurality of blood exhaust apertures is defined by an inner aperture edge and an outer aperture edge, the inner aperture edge including one of a rounded edge portion and a chamfered edge portion. The pump housing component may be composed of a metal in accordance with implementations. In some implementations, the pump housing component is electropolished. The chamfered edge portions of circumferential aperture surfaces may be formed via tumbling, rolling, and machining or material removal or any other suitable fabrication process, such that the circumferential aperture surface is rounded, at least in part, in a region of the inner edge or the outer edge. Prior to rounding a portion of the inner edge or outer edge, the circumferential aperture surface and the inner surface or outer surface 108 may include an edge configured at a 90-degree angle or chamfered. Accordingly, the inner or outer edge may be rounded or chamfered to remove a right-angled edge.

As utilized herein, the terms "approximately," "about," "substantially" and similar terms are intended to have a broad meaning in harmony with the common and accepted usage by those of ordinary skill in the art to which the subject matter of this disclosure pertains. It should he understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

It is important to note that the constructions and arrangements of apparatuses or the components thereof as shown in the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative implementations. Other substitutions, modifications, changes and omissions may also be made in the design, operating conditions and arrangement of the various exemplary implementations without departing from the scope of the present disclosure.

While various inventive implementations have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive implementations described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be implemented as a method, of which at least one example has been provided. The acts performed as part of the method may be ordered in any suitable way unless otherwise specifically noted. Accordingly, implementations may be constructed in which acts are performed in an order different than illustrated, which may include performing some acts simultaneously, even though shown as sequential acts in illustrative implementations.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of" and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

The invention claimed is:

1. A blood pump assembly comprising:
    a pump;
    an impeller having one or more blades, the pump being configured to drive the impeller in rotation; and
    a pump housing component sized for passage through a body lumen and coupled to the pump, the pump housing component including a peripheral wall extending about a rotation axis of the impeller, the peripheral wall having:
        an inner surface,
        an outer surface, and
        a plurality of blood exhaust apertures, each blood exhaust aperture being defined by an inner edge and an outer edge between the inner surface and the outer surface; and
        wherein the inner edge of each blood exhaust aperture has a rounded portion, and the outer edge of each blood exhaust aperture has a chamfered portion.

2. The blood pump assembly of claim 1, wherein the one or more blood exhaust apertures are circular-shaped.

3. The blood pump assembly of claim 1, wherein the outer edges of each blood exhaust apertures further includes a rounded portion.

4. The housing of claim 3, wherein each rounded portion of the inner edge of each blood exhaust aperture has a radius of about 105 microns or greater.

5. The housing of claim 1, wherein each rounded portion of the inner edge of each blood exhaust aperture has a radius of about 40 microns or greater.

6. The housing of claim 1, wherein the entirety of the inner edge of each blood exhaust aperture is rounded.

7. The blood pump assembly of claim 1, wherein the plurality of blood exhaust apertures comprises at least six blood exhaust apertures.

8. The blood pump assembly of claim 1, wherein the impeller is positioned at least in part in the pump housing component.

9. The blood pump assembly of claim 1, wherein the pump housing component is coupled to the pump at a first end and the pump housing component is coupled to a cannula component at a second end opposite the first end.

10. The blood pump assembly of claim 9, wherein the cannula component includes a blood inlet manifold.

11. The blood pump assembly of claim 10, further comprising a pigtail extension coupled to the blood inlet manifold.

12. The blood pump assembly of claim 1, wherein the housing component is composed of a metal.

13. The blood pump assembly of claim 1, wherein the pump housing component is electropolished.

14. The blood pump assembly of claim 1, wherein for each blood exhaust aperture, the rounded portion of the inner edge transitions into a rounded portion of the outer edge, the rounded portion of the inner edge and the rounded portion of the outer edge having the same radius and center of curvature.

15. A blood pump assembly comprising:
- a pump;
- an impeller having one or more blades, the pump being configured to drive the impeller in rotation; and
- a pump housing component sized for passage through a body lumen and coupled to the pump, the pump housing component including a peripheral wall extending about a rotation axis of the impeller, the peripheral wall having:
  - an inner surface,
  - an outer surface, and
  - a plurality of blood exhaust apertures positioned radially equidistant from a fixed longitudinal point along the rotation axis, each blood exhaust aperture being defined by an inner edge and an outer edge between the inner surface and the outer surface; and
- wherein the inner edge of each blood exhaust aperture has a rounded portion, and the outer edge of each blood exhaust aperture has a chamfered portion.

* * * * *

UNITED STATES PATENT AND TRADEMARK OFFICE
CERTIFICATE OF CORRECTION

PATENT NO. : 11,364,373 B2
APPLICATION NO. : 16/937023
DATED : June 21, 2022
INVENTOR(S) : Scott C. Corbett, Zhongwei Qi and Kar Lee Page 1 of 1

It is certified that error appears in the above-identified patent and that said Letters Patent is hereby corrected as shown below:

In the Claims

Claim 3, Column 12, Line 46:
Now reads: "each blood exhaust apertures"; should read -- each blood exhaust aperture --

Claim 4, Column 12, Line 48:
Now reads: "housing of claim 3"; should read -- housing of claim 1 --

Claim 4, Column 12, Line 50:
Now reads: "about 105 microns"; should read -- about 40 microns --

Claim 5, Column 12, Line 51:
Now reads: "housing of claim 1"; should read -- housing of claim 3 --

Claim 5, Column 12, Line 53:
Now reads: "about 40 microns"; should read -- about 105 microns --

Signed and Sealed this
First Day of November, 2022

Katherine Kelly Vidal
*Director of the United States Patent and Trademark Office*